United States Patent [19]

Krenitsky et al.

[11] Patent Number: 5,059,604
[45] Date of Patent: Oct. 22, 1991

[54] 2-AMINO PURINE DERIVATIVES

[75] Inventors: Thomas A. Krenitsky, Chapel Hill; Lilia M. Beauchamp, Raleigh, both of N.C.

[73] Assignee: Burroughs Wellcome Co., Research Triangle Park, N.C.

[21] Appl. No.: 574,555

[22] Filed: Jan. 27, 1984

Related U.S. Application Data

[63] Continuation-in-part of Ser. No. 434,394, Oct. 14, 1982, abandoned.

[51] Int. Cl.$^5$ .................... C07D 473/18; A61K 31/52
[52] U.S. Cl. ..................................... 514/261; 544/276; 544/277
[58] Field of Search ................. 544/277, 276; 424/253

[56] References Cited

U.S. PATENT DOCUMENTS 4,199,574  4/1980  Schaeffer ........................... 544/276
4,323,573  4/1982  Schaeffer ........................... 544/277

Primary Examiner—Nicholas Rizzo
Attorney, Agent, or Firm—Donald Brown; Lawrence A. Nielsen

[57] ABSTRACT

A group of 2-aminopurine compounds, which have in the 6-position a hydrogen and in the 9-position an acyclic moiety

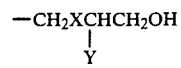

wherein X is oxygen or sulphur and Y is hydrogen or $CH_2OH$ (provided than when X is oxygen Y may not be hydrogen), are converted enzymatically in vivo into the corresponding 6-hydroxy (i.e. guanine) derivatives which are potent antiviral compounds. The enzymatic conversion may also be effected ex vivo (i.e. in vitro) as a method of synthesizing the corresponding 6-hydroxy derivatives.

14 Claims, No Drawings

2-AMINO PURINE DERIVATIVES

This application is a continuation-in-part of our co-pending application Ser. No. 434,394, filed Oct. 14, 1982, abandoned.

The present invention relates to antiviral purine derivatives containing an acyclic chain in the 9-position.

U.K. Patent Specification No. 1523865 and U.S. Pat. No. 4,199,574 describe a broad class of purine derivatives containing an acyclic side chain in the 9-position. These purine derivatives have been found to have antiviral activity against various classes of DNA viruses particularly against herpes viruses such as herpes simplex.

Among these derivatives, 9-(2-hydroxyethoxymethyl)guanine (otherwise known as acyclovir) has been found to have particularly good activity against herpes viruses such as herpes simplex. However, while acyclovir has been found to be especially effective upon topical or parenteral administration, it is only moderately well absorbed upon oral administration with corresponding levels of drug in the plasma. It will be appreciated that when one is treating an internal disorder by oral administration of a drug, it is clearly desirable that the drug should be well absorbed from the gastro-intestinal tract with resulting high plasma levels.

The surprising discovery has now been made that a certain class of purine derivatives, falling within the scope of the compounds broadly described in U.K. Patent Specification No. 1523865 and characterized by the presence of a hydrogen atom in the 6-position of the purine nucleus, can be readily converted in vivo by the action of the molybdo-flavo-protein enzymes xanthine oxidase/dehydrogenase or aldehyde oxidase into the corresponding 6-hydroxy purine derivative acyclovir. Furthermore, from experiments in rats, it has been found that oral administration of such 6-hydrogen derivatives results in efficient absorption from the gastro-intestinal tract and high plasma levels of the corresponding 6-hydroxy compound, formed by enzymatic conversion of the 6-hydrogen compound.

Also, for example, the 6-hydrogen purine derivatives are considerably more soluble in water than the corresponding 6-hydroxy compounds. This improved water-solubility enables the 6-hydrogen compounds to be used in a greater variety of aqueous pharmaceutical formulations which require some solubilisation of the drug.

The above-mentioned class of 6-hydrogen purine analogues may be represented by the formula (I)

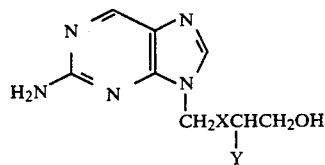

(wherein X represents an oxygen or sulfur atom and Y represents a hydrogen atom or a hydroxymethyl group provided that Y may not be hydrogen when X is oxygen) and physiologically acceptable salts thereof.

Salts of the compounds of formula (I) which may be conveniently used in therapy include physiologically acceptable salts of organic acids such as lactic, acetic, malic or p-toluenesulphonic acid as well as physiologically acceptable salts of mineral acids such as hydrochloric or sulphuric acid.

In a mouse herpes simplex encephalitis model the compound of formula (I) wherein X represents an oxygen atom and Y represents a hydroxymethyl group was shown to have unexpected and remarkably superior activity compared with the corresponding 6-hydroxy compound.

The discovery that the 6-hydrogen purines of formula (I) above can be readily converted into their corresponding 6-hydroxy analogues is surprising since in previous studies with xanthine oxidase from bovine milk (H. Lettre et al. (1967) Biochem. Pharmacol., 16, 1747-1755; T. A. Krenitsky et al. (1972) Arch. Biophys., 150, 585-599) it was shown that 9-substitution obliterates or greatly diminishes the rate at which a variety of purines are oxidized. In view of these observations, it was surprising to find that this enzyme oxidized for example 2-amino-9-[(2-hydroxy-1-hydroxymethylethoxy)methyl]-9H-purine, a 9-substituted derivative of 2-aminopurine, at a faster rate than the 9-unsubstituted purine, as established from enzyme studies.

The high level of absorption of the compounds of formula (I) from the gastrointestinal tract renders the compounds especially useful when oral administration of the compounds is desired, e.g. in the treatment of diseases caused by various DNA viruses, such as herpes infections for example herpes simplex, varicella or zoster, cytomegalovirus as well as diseases caused by hepatitis B or Epstein-Barr virus. The compounds of formula (I) can also be used for the treatment or prophylaxis of papilloma or wart virus infections. In addition to their use in human medical therapy the compounds of formula (I) can be administered to other animals for the treatment or prophylaxis of viral diseases, e.g. in other mammals. For example, those compounds of formula (I) wherein Y represents a hydroxymethyl are especially useful for the treatment of equine rhinopneumonitis. By administration of a compound of formula (I) or physiologically acceptable salt thereof, especially by the oral route, it is possible to achieve an advantageous effect against such disorders.

According to a further feature of the present invention there are provided the compounds of formula (I) and physiologically acceptable salts thereof for use in the treatment or prophylaxis of a viral disease in an animal, e.g. a mammal such as man.

The present invention also provides a method for the treatment or prophylaxis of a viral disease in an animal, e.g. a mammal such as man which comprises administering to the animal an effective antiviral amount of a compound of formula (I) or a physiologically acceptable salt thereof.

The compounds of formula (I) and the physiologically acceptable salts thereof (hereafter collectively referred to as the active ingredients) may be administered by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with for example the condition of the recipient.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable, effective dose will be in the range 0.1 to 250 mg per kilogram body weight of recipient per day, preferably in the range 1 to 100 mg per kilogram body weight per day and most preferably in the range 5 to 20 mg per kilogram body weight per day; an optimum dose is about 10 mg per kilogram body weight per day. (Unless otherwise indicated all weights of active ingredient are calculated as the parent compound of formula (I): for salts thereof the figures would be increased proportionately.) The desired dose is preferably presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

While it is possible for the active ingredients to be administered alone it is preferable to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl mono-stearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solution which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The present invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

For oral administration the compositions can be in the form of a tablet, granule, drench, paste, cachet, capsule or feed supplement. Granules may be made by the well known techniques of wet granulation, precompression or slugging. They can be administered to animals in an inert liquid vehicle so as to form a drench, or in a suspension with water or oil base. Preferably further accessory ingredients such as a dispensing agent are included. These formulations preferably contain from 15 to 85% of the active ingredient.

A paste may be formulated by suspending the active ingredient in a liquid diluent. A stiffening or thickening agent may be included together with a wetting agent or a humectant if the liquid is water. If an emulsion paste is needed then one or more surface active agents should desirably be included. From 25 to 80% weight of these paste formulations may comprise the active ingredient.

In feed supplements the active ingredient is generally present in large amounts relative to the accessory ingredients, and the supplements may be added directly or after intermediate blending or dilution. Examples of accessory ingredients for such formulations include solid, orally ingestible carriers such as corn meal, soya flour, wheat shorts, soya grits, edible vegetable materials and fermentation residues. The active ingredient is usually incorporated in one or more of the accessory ingredients and intimately and uniformly dispersed by grinding, tumbling or stirring with conventional apparatus. Formulations containing 1 to 90% by weight of the active ingredient are suitable for adding to feeds.

For the treatment of herpes infections in horses, an oral or parenteral dose of from 0.1 to 250 mg per kg body weight per day, preferably from 2 to 100 mg per kg per day may be required. The dose may be split up into discrete units administered at regular intervals during the day, and repeated daily for up to 14 days or until the infection is cleared. For viral infections in other animals the dose may vary depending on the size and metabolism of the animal. The compositions may be administered in unit dosage form, such as a tablet a few times daily in the amount of 10 to 1000 mg per unit dose.

The compounds of formula (I) and physiologically acceptable salts thereof may be prepared in conventional manner by analogous processes for preparing compounds of similar structure, such as those methods described in U.K. Patent Specification No. 1523865.

The present invention further provides a process for the preparation of the compounds of formula (I) and physiologically acceptable salts thereof (provided that when $Y^1$ or Y is a hydrogen atom X may not be an oxygen atom) which comprises:

a) deblocking a compound of formula (II)

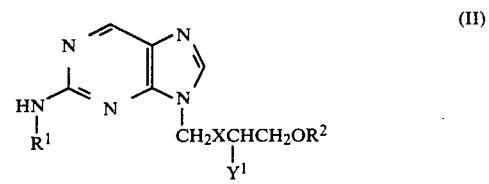

(II)

(wherein X is as defined above, $R^1$ and $R^2$, which may be the same or different, each represents a hydrogen atom or a blocking group, and $Y^1$ represents a hydrogen atom or a group of formula —$CH_2OR^3$ (wherein $R^3$ represents a hydrogen atom or a blocking group) providing that at least one of $R^1$, $R^2$ and $R^3$ represents a blocking group) to form a compound of formula (I) or a physiologically acceptable salt thereof;

b) converting a compound of formula (III)

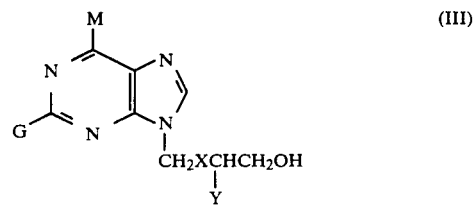

(III)

(wherein X and Y are as defined above, M represents a hydrogen atom or a group or atom convertible into a hydrogen atom and G represents a group or atom convertible into an amino group or (when M is other than a hydrogen atom) G may alternatively represent an amino group) or a salt thereof into a compound of formula (I) or a physiologically acceptable salt thereof;

c) reacting a compound of formula (IV)

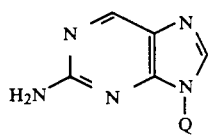
(IV)

(wherein Q represents a leaving atom or group) with a compound of formula (V)

$$ACH_2OCHCH_2B \atop Y \qquad (V)$$

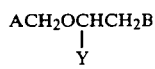

(wherein X and Y are as defined above, A represents a leaving group or atom and B represents an optimally protected OH group);

d) closing a ring in a precursor compound having either the pyrimidine or imidazole ring incompletely formed;

e) reducing a compound of formula (VI)

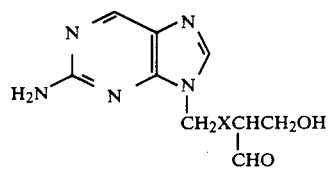
(VI)

(wherein X is as defined above) or a salt thereof to form a compound of formula (I) (wherein Y represents a hydroxymethyl group) or a physiologically acceptable salt thereof; or g) hydrolysing a compound of formula (VII)

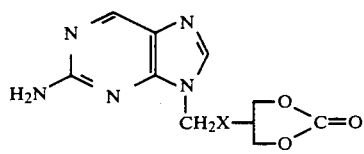
(VII)

(wherein X is as defined above) or a salt thereof to form a compound of formula (I) (wherein Y represents a hydroxymethyl group) or a physiologically acceptable salt thereof, and optionally effecting one or more of the following conversions, in any desired sequence:

i) where the resulting product is a base, converting the said base into a physiologically acceptable acid addition salt thereof;

ii) where the resulting product is an acid addition salt, converting the said salt into the parent base;

In method a) the blocking groups $R^1$, $R^2$ and $R^3$ may be selected for example from acyl groups such as $C_{1-4}$ alkanoyl groups e.g. acetyl, or aroyl groups, e.g. benzoyl; arylmethyl groups e.g. benzyl; or tri-$Cl_{1-4}$ alkylsilyl e.g. trimethylsilyl. Arylmethyl blocking groups may be removed for example by hydrogenolysis, e.g. by hydrogenation in the presence of Raney nickel or palladium catalyst or by the use of sodium in liquid ammonia. Acyl blocking groups may be removed for example by hydrolysis using for example an amine such as methylamine or triethylamine, advantageously in an aqueous medium. Trialkylsilyl blocking groups may be removed for example by solvolysis e.g. with alcoholic or aqueous ammonia, or by alcoholysis.

Conversion of a compound of formula (III) into a compound of formula (I), by method b), can be achieved by various means. For example G may represent an azide group which can be reduced to an amino group by catalytic hydrogenation using a suitable catalyst such as palladium. Alternatively, G may represent a halogen atom or an alkylthio or alkylsulphonyl group which can be converted to an amino group by aminolysis using for example ammonia. Also, M may represent a halogen atom or a mercapto group which can be converted into a hydrogen atom by reduction or dethiolation respectively, both in conventional manner.

These processes together with other conventional processes are described in Fused Pyrimidines, Part II, Purines Ed. by D. J. Brown (1971), Wiley-lnterscience.

In process (c), the group Q in formula (IV) may for example represent a hydrogen atom; an acyl group, e.g. a $C_{1-4}$ alkanoyl group such as an acetyl group or an aroyl group such as a benzoyl group; or a tri-$C_{1-4}$ alkylsilyl group such as a trimethylsilyl group. The group A in formula (V) may for example represent a halogen atom (e.g. chlorine) or an acyloxy group wherein the acyl moiety may be for example a $C_{1-4}$ alkanoyl group such as acetyl, or an aroyl group such as benzoyl. The reaction may be conveniently effected in a strong polar solvent such as dimethylformamide or hexamethylphosphoramide, advantageously in the presence of a base such as triethylamine or potassium carbonate. Alternatively, a thermal condensation may be effected by heating the compounds of formulae (IV) and (V) in the presence of a catalytic amount of a strong acid, e.g. sulphuric acid.

Process d) involves the ring closure of either the imidazole or pyrimidine ring to give the final product. In the case of the imidazole ring this may be achieved by reaction of an appropriate precursor with a $C_1$ reagent, such as triethylorthoformate, under for example mildly acidic conditions, at a temperature of about 25° C., for several hours. A suitable precursor is a substituted pyrimidine of formula (VIII)

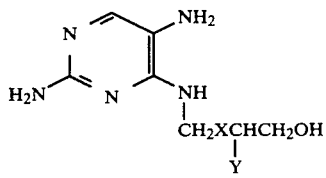
(VIII)

An alternative reagent is diethoxymethyl acetate, when neutral conditions at about 100° C. for about 10-15 minutes are preferred.

Reduction of a compound of formula (VI) in process (e) may be achieved for example by reaction with an appropriate aldehyde reducing agent such as sodium borohydride, sodium cyanoborohydride, tetraethylammonium borohydride or pyridine/diborane/tetrahydrofuran/ trifluoroacetic acid.

In process (g), hydrolysis of the compound of formula (VII) may be effected for example under basic conditions, e.g. by treatment with an organic amine such as methylamine or triethylamine.

The following Examples illustrate the present invention.

EXAMPLE 1

2-Amino-9-(2-hydroxyethylthiomethyl)purine

A 1 liter round bottom flask equipped with a magnetic stirring bar and a $CaCl_2$ drying tube was charged with 5.0 g (29.50 mM) 2-amino-6-chloro-purine, 6.8 g (29.50 mM) 2-(chloromethylthio)ethyl benzoate, 4.07 g (Z9.50 mM) potassium carbonate and 750 ml of anhydrous dimethylformamide. The reaction was stirred at room temperature for 16 hours after which time another 2.0 g (8.7 mM) of 2-(chloromethylthio)ethyl benzoate along with 1.2 g (8.7 mM) potassium carbonate were added and stirring continued for an additional 24 hours at room temperature. The reaction mixture was then filtered through a pad of Celite in a sintered glass funnel and rotary evaporated in vacuo to a viscous yellow oil. The oil was adsorbed on to 20.0 g of Merck silica gel 60 (70–230 mesh) and this predesorbed phase applied to the top of a column of Merck silica gel 60 (230–400 mesh). Elution of the column using 6:4 ethyl acetate-benzene provided 2-amino-9-(2-benzoyloxyethylthiomethyl) -6-chloro-purine as an off-white solid as a single material by TLC on silica gel 8:2 ethyl acetate-hexane. $^1$H NMR, $CDCl_3$ 8.0–7.15$\delta$, 6H, multiplet; 5.1$\delta$, 4H, broad singlet; 4.5$\delta$, 2H, triplet; 2.98$\delta$, 2H, triplet. This product (0.98 g, 2.70 mM) was placed into a 500 ml Parr hydrogenator bottle together with 2.5 g $Pd(OH)_2$ catalyst, 50 ml $Et_3N$ and 200 ml of methanol. This was shaken of a Parr hydrogenator under 50 p.s.i. hydrogen for 16 hours at room temperature. TLC of the hydrogenolysis product on silica gel with 8% methanol-ethyl acetate showed only partial reaction. The catalyst was removed by filtration through a pad of Celite in a sintered glass funnel, 2.0 g of fresh $Pd(OH)_2$ catalyst and 7.0 ml triethylamine were added and the reaction mixture again shaken under 50 p.s.i. hydrogen for 20 hours. At this point t.l.c. showed the reaction to be complete, the catalyst was removed as before and the methanol rotary evaporated in vacuo to give a clear glass, which was taken up into 100 ml of 1:1 methanol-water containing 20% methylamine. The resulting solution was stirred at room temperature for 4 hours and rotary evaporated in vacuo to give an amorphous solid. The solid was adsorbed on to 10.0 g of 70–230 mesh Merck silica gel 60 and this preadsorbed phase applied to the top of a column of 230–400 mesh Merck silica gel 60. Elution of the column using 10% methanol ethyl acetate provided a solid that crystallised from ethyl acetate-hexane to give the title compound in the form of tiny needles, mp. 122–124° C, t.l.c. : 1 spot on silica gel with 15% methanol:ethyl acetate $^1$H NMR dmso-d6 8.59$\delta$, 1H singlet; 8.15$\delta$, 1H singlet; 6.56$\delta$, 2H broad singlet; 5.24$\delta$, 2H singlet; 4.83$\delta$, 1H triplet; 3.49$\delta$, 2H multiplet; 2.69$\delta$, 2H multiplet; Anal. Theory C: 42.65, H: 4.92, N: 31.09 found C: 42.70, H: 4.94, N: 31.04.

EXAMPLE 2 a)

2-Amino-9-(2-benzoyloxy-1-(benzoyloxymethyl)ethoxy)methyl-6-chloro-9H-purine A mixture of 7.0 g (41.2 mM) of 2-amino-6-chloropurine, 4.55 g (34.4 mM) of ammonium sulfate, and 200 ml hexamethyldisilazane were combined under nitrogen and refluxed wih stirring for five hours. The mixture was flash evaporated, followed by the addition of 8.8 g (23.6 mM) of 2-0-(acetylmethyl)-1,3-bis-(0-benzoyl)-glycerol in about 10 ml benzene. The mixture was heated for 1.5 hours in an oil bath and under aspirator pressure with a distilling head hookup. Then the mixture was cooled to room temperature. Methanol was added to the mixture which was placed over a steam bath for 30 minutes. Next, the mixture was washed with $H_2O$ and extracted 3 times with ethyl acetate and the organic layer dried over anhydrous magnesium sulphate for about 30 minutes. The mixture was then filtered, the salt washed with ethyl acetate and then flash evaporated.

Flash column chromatography with 6:1 $CH_2Cl_2$/acetone eluent yielded the title compound as an analytically pure product, a white solid with a mpt. of 130°–131°.

b)

2-Amino-9-[(2-benzoyloxy-1-benzoyloxymethyl)ethoxy)methyl]-9H-purine

A mixture of 3,393 g (7.04 mM) of 2-amino-9[(2-benzoyloxy-1-(benzoyloxymethyl)ethoxy)methyl]-6--chloro-9H-purine, 100 ml ethanol, 100 ml tetrahydrofuran and 1.9 ml triethylamine was added to 0.6 g Pd-C catalyst in a Parr bottle. The mixture was shaken under 50 P.S.I of $H_2$ for 24 hours. The Pd-C was filtered through a Celite pad and 0.65 g fresh Pd-C was added to the reaction mixture and the hydrogenation was continued for 4 days. Column chromatography using 100% $CH_2Cl_2$, 4:1 $CH_2Cl_2$/acetone, and 100% acetone produced the title compound, mpt. 132°–133° C.

EXAMPLE 3

2-Amino-9-[(2-hydroxy-1-hydroxymethylethoxy)methyl]-9H-purine

A mixture of 0.844 g (1.88 mM) of 2-amino-9-[(2-benzoyloxy-1-benzoyloxysethylethoxy)methyl]-9H-purine and 100 ml of a 40% aqueous methylamine solution was stirred at room temperature for 30 minutes. The mixture was flash evaporated to a yellow oil which was then washed with water. The aqueous layer was then extracted twice with methylene chloride. The aqueous layer containing the product was then flash evaporated to a light yellow oil. Recrystallization of the oil in hot acetonitrile yielded the title compound as an analytically pure ivory solid mpt. 148°–151°.

The following Examples 4 to 8 illustrate pharmaceutical formulations according to the invention where the active compound is a compound of formula (I) or a physiologically acceptable salt thereof.

EXAMPLE 4

Tablet

| | |
|---|---|
| Active compound | 100 mg |
| Lactose | 200 mg |
| Starch | 50 mg |
| Polyvinylpyrrolidone | 5 mg |
| Magnesium stearate | 4 mg |
| | 359 mg |

Tablets were prepated from the foregoing ingredients by wet granulation followed by compression.

EXAMPLE 5

Injectable Solution

| Active compound | 0.775 g |
|---|---|
| Sterile, pyrogen-free, pH 7 phosphate buffer to | 25 ml |

EXAMPLE 6

Ophthalmic Solution

| Active compound | 1.0 g |
|---|---|
| Sodium chloride, analytical grade | 0.9 g |
| Thiomersal | 0.001 g |
| Purified water | to 100 ml |
| pH adjusted | to 5.5–7.5 |

EXAMPLE 7

Oil Based Paste

| China Clay (solid diluent) | 20.0% w/w |
|---|---|
| Mineral Oil* (liquid diluent) | 60.0% w/w |
| Active compound | 20.0% w/w |

*Mineral oil is a high boiling fraction of a refined petroleum oil containing not less than 96% unsulphonatable material.

The components were mixed to provide a paste of uniform consistency.

EXAMPLE 8

Feed Supplement—Pellets

| Active compound | 1% |
|---|---|
| Cereal Base | 99% |

The two ingredients were mixed then fed to any conventional feed stuff pelleting plant.

We claim:

1. A pharmaceutical composition comprising an effective antiviral amount of the compound of the formula

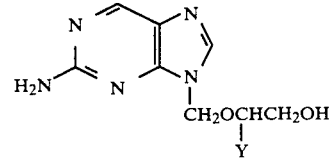

where Y is hydroxymethyl or a pharmacologically acceptable salt thereof and a pharmacologically acceptable carrier therefor.

2. A method of treating a viral infection in a mammal comprising administration to said mammal of the compound of the formula

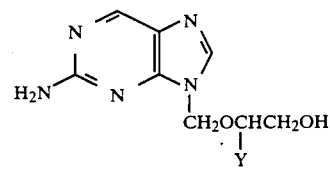

where Y is hydroxymethyl or a pharmacologically acceptable salt thereof.

3. The method of claim 2 in which the viral infection is caused by hepatitus B virus.

4. The method of claim 2 in which the viral infection is caused by the Epstein-Barr virus.

5. The method of claim 2 in which the viral infection is caused by warts.

6. The method of claim 2 in which the virus infection is a herpes virus infection.

7. The method of claim 2 in which the infection is a cytomeglovirus infection.

8. The method of claim 2 in which the infection is a papilloma infection.

9. The method of claim 2 in which the infection is a varicella infection.

10. The method of claim 2 in which the infection is a herpes simplex infection.

11. The method of claim 2 in which the infection is a zoster infection.

12. The composition of claim 1 in the form of a tablet or capsule.

13. The composition of claim 1 in a sterile form for parenteral administration.

14. A compound of the formula

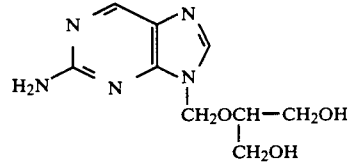

or a physiologically acceptable salt thereof.

* * * * *